United States Patent [19]
Chimento

[11] Patent Number: 5,270,035
[45] Date of Patent: Dec. 14, 1993

[54] HAIR CONDITIONER CONTAINING DISODIUM COCOAMPHODIACETATE

[75] Inventor: Samuel V. Chimento, Simi Valley, Calif.

[73] Assignee: Lexin International Marketing Corporation, San Carlos, Calif.

[21] Appl. No.: 886,362

[22] Filed: May 21, 1992

[51] Int. Cl.$^5$ ............................................. A61K 7/075
[52] U.S. Cl. ......................................... 424/70; 424/71
[58] Field of Search ................... 424/70; 514/781; 252/DIG. 13

[56] References Cited

U.S. PATENT DOCUMENTS

| | | | |
|---|---|---|---|
| 4,205,063 | 5/1980 | Khalil et al. | 514/781 |
| 5,053,230 | 10/1991 | Gazzani | 424/70 |
| 5,112,603 | 5/1992 | Nadolsky et al. | 424/70 |

Primary Examiner—Thurman K. Page

[57] ABSTRACT

A hair treatment composition for giving hair a thicker appearance includes between 0.25% and 5.0% by weight of Disodium Cocoamphodiacetate. Other ingredients such as astringents, nutrients, herb extracts, and preservatives enhance the effectiveness of the composition.

7 Claims, No Drawings

HAIR CONDITIONER CONTAINING DISODIUM COCOAMPHODIACETATE

FIELD OF INVENTION

The present invention relates to a new mixture of ingredients for conditioning human hair.

BACKGROUND OF THE INVENTION

Human hair consists of a root embedded in the skin and a shaft projecting from the skin surface. The root ends in the hair bulb which is a soft, whitish enlargement. The bulb is lodged in an elongated pit in the skin, called the follicle. If the hair is long, the follicle extends into the subcutaneous fatty tissue beneath the skin. At the base of each follicle is a conical swelling called the papilla. The papilla and follicle are supplied with nerves and blood vessels. Hair growth takes place at the junction of the follicle and the papilla. As the cells are pushed up the follicle, they harden and become the hair strand.

A small muscle is attached to each hair follicle. If the muscles are contracted, the hairs become more erect and the follicles are dragged upward, producing small bumps on the surface of the skin, called gooseflesh. Sebaceous (fat) glands attached to each hair release sebum which lubricates the hair. Excess sebum tend to make the hair look unsightly.

Hair growth is not a continuous process, but progresses for a variable period and then stops. The approximate 150,000 hairs of the scalp are able to grow for years without interruption. Baldness, or alopecia, occurs because of a natural tendency of the follicles of the scalp to become very small as humans age/Common baldness is hereditary and occurs more frequently in men than in women. Good grooming and hygiene are essential in providing healthy and good-looking hair and various aids and agents are available to help in achieving this status.

The basic cleaning agents in soaps and detergents are called surface-active agents, or surfactants When added to a liquid, they reduce its surface tension (the affinity that the surface molecules have for each other), thereby increasing the liquid's spreading and wetting properties. Part of the surface-active molecule must be hydrophilic, or "water-loving", and part must be hydrophobic, or water-repellent. Surface-active molecules concentrate at the interfaces, or areas of contact, between water and oil. One end of the molecule seeks the water; the other end seeks oil (or air, if the interface is between water and air). At water-oil interfaces, surface-active against emulsify oil--they mix it into the liquid the wa fat is mixed in milk; at water-air interfaces, they trap air molecules to produce foam.

There have been many attempts to create a solution which when applied to the hair, creates a thicker more abundant look even though no new hair growth is created. Moreover, there have been many attempts to create a mixture which when applied to the hair, changes or corrects the chemistry of the hair.

See, for example, U.S. Pat. No. 4,136,188, "Treating Hair with Cosmetic Formulations containing Polypeptides", which attempts to correct the pH balance of the chemistry of human hair after it has been altered by another cosmetic treatment.

Many other formulations for improving the condition of human hair contain various surfactants. See, for example, U.S. Pat. Nos. 4,964,874 for "Hair Treatment Product; Cationic Surfactant, Fatty, Alcohol and Dye Mixture"; compare, 4,855,130 for "Hair Treating Compositions and Processes for Improving the Condition of Hair; Synergistic Mixture of Glycerin and Organic Acid".

In general, hair conditioning treatments may also contain in addition to surfactants and synthetic polymers, thickeners, antioxidants, organic acids, perfume oils and other ingredients. See, for example, U.S. Pat. Nos. 4,752,467 for "Hair Treatment Agent and Method for Improving the Condition of Hair; Mixture of Trimethyl Ammonia Acetate Betaine and Organic Acid" and 4,726,945 for "Hair Rinse Conditioner; Mixture of Quaternary Ammonium Compound, Alkylamidodiakylamine, Propylene Glycol, Mineral Oil, Fatty Alcohol and Siloxane".

INCORPORATION BY REFERENCE

The complete disclosure of each of the U.S. Patents discussed above, namely U.S. Pat. Nos. 4,136,188; 4,964,874; 4,855,130; 4,752,467; and 4,726,945 is incorporated herein by reference.

SUMMARY OF THE INVENTION

It is an object of the present invention to provide a mixture of ingredients in an aqueous solution which when applied to human hair, adds body and the appearance of thickness to the hair. This object is desirable to people with thin looking hair or with smaller quantities of hair such as people who have lost hair due to genetics or other conditions which result in the temporary or permanent loss of hair.

This object is achieved by a solution containing Disodium Cocoamphodiacetate (DSC), a surfactant. Moreover, this object is achieved by mixing Disodium Cocoamphodiacetate in an aqueous mixture with one or more astringents, cleaning agents, emulsifiers, and adjuvants. For example, Panthenol, Polysorbate 80, Polyquarternium-11, Inositol, Glycerin, and natural extracts may be used. As will be described below, a variety of ingredients has been found useful as well and a preferred embodiment of the inventive mixture may contain as many as 25 individual ingredients in small amounts.

DESCRIPTION OF THE PREFERRED EMBODIMENTS

It has been found through careful study and trials that an effective amount of Disodium Cocoamphodiacetate when applied in solution to human hair enhances the appearance of the hair, in particular by making it look thicker.

Insofar as Disodium Cocoamphodiacetate is a surfactant and thus a cleansing agent, the present invention is aimed at cleansing hair follicles and scalp and removing excess sebum as well. A particularly useful hair treatment composition of the invention for giving hair a thicker appearance comprises in an aqueous base, Disodium Cocoamphodiacetate, and at least one of a fat/sebum emulsifier, a surfactant, and a natural astringent cleansing material. The aqueous component suitably ranges from 70-95% depending on the other ingredients employed.

Moreover, it has been found that the addition of an effective amount of Panthenol, preferably in the form of Calcium Pantothenate, Polysorbate 80, Polyquarternium-11, Inositol, and natural extracts enhance the effect of the invention by invigorating the scalp and follicles. For example, there may be additionally present one or more of the following in the amounts indicated:

up to 2.0% by weight Panthenol,
up to 2.0% by weight Polysorbate 80,
up to 2.0% by weight Polyquarternium-11,
up to 2.0% by weight Inositol, and
up to 15% by weight of a natural herb extract.

The DSC is conveniently and suitably present in the composition in the range of from 0.25% to 5% by weight, but preferably between 0.75% to 1.25% by weight. The remainder of the ingredients can range up to 20–25% depending upon the particular ones used.

Through a number of trials and careful study, a composition containing the ingredients in Table 1 below has been found to be quite effective in achieving the objects of this invention.

TABLE 1

| Ingredient | Weight % | Activity of the Ingredient |
| --- | --- | --- |
| Disodium Cocoamphodiacetate | 1.0% | surfactant/dressing |
| Inositol | 1.0% | fat/sebum emulsifier |
| Panthenol | 1.0% | hair thickener |
| Polyquarternium-11 | 1.0% | adds body |
| Polysorbate 80 | 1.0% | surfactant/dressing |
| Sage extract | 1.0% | astringent/cleansing lotion |
| Deionized purified water | balance | base |

Moreover, it has been found that the addition of certain astringents and nutrients to the solution further enhance its effectiveness. For example, herb extracts in a glycol base add astringency and cleansing properties. A hair treatment composition as claimed in claim 5 wherein the astringent is one or more of those selected from the group consisting of Nettle extract, Yarrow extract, Coltsfoot extract, Rosemary extract, Birch sap, Clover blossom extract, Birch leaf extract, Horsetail extract, and Sage extract. Below, in Table 2, is a list of ingredients in a preferred embodiment of the invention.

TABLE 2

| Ingredient | Weight % | Activity of the Ingredient |
| --- | --- | --- |
| Glycerin | 0.5% | reduces friction, adds luster |
| Panthenol (Ca Pantothenate) | 2.0% | thicker looking hair |
| Polysorbate 80 | 1.0% | surfactant/dressing |
| Disodium Cocoamphodiacetate | 1.0% | surfactant/dressing |
| Glutamic Acid | 1.0% | healthy for hair and scalp |
| Polyquarternium-11 | 1.0% | adds body |
| Ethoxydiglycol | 1.0% | carrier for herb extract |
| Propylen glycol | 1.0% | carrier for herb extract |
| Butylene glycol | 1.0% | carrier for herb extract |
| Nettle extract | 1.0% | astringent/cleansing lotion |
| Yarrow extract | 1.0% | astringent/cleansing lotion |
| Coltsfoot extract | 1.0% | astringent/cleansing lotion |
| Rosemary extract | 1.0% | astringent/cleansing lotion |
| Birch sap | 1.0% | astringent/cleansing lotion |
| Clover blossom extract | 1.0% | astringent/cleansing lotion |
| Birch leaf extract | 1.0% | astringent/cleansing lotion |
| Horsetail extract | 1.0% | astringent/cleansing lotion |
| Sage extract | 1.0% | astringent/cleansing lotion |
| Inositol | 1.0% | fat/sebum emulsifier |
| DMDM Hydantoin | 0.25% | preservative |
| Methylparaben | 0.2% | preservative |
| Propylparaben | 0.033% | preservative |
| Methly nicotinate | <1% | healthy for hair and scalp |
| Deionized purified water | balance | base |

Methyl nicotinate has been found to improve the appearance of the hair.

The compositions of the invention are thin, watery materials that are easily applied. In use, several milliliters of the composition of the invention are vigorously applied into the scalp and hair for several minutes. It is preferably left on and not washed off. Good results are obtained when the composition is applied at night and left on overnight. It may then be washed out in the morning and replaced before the daily activities are begun. I is preferred that application of the material be repeated one to three times during the day.

Although the invention is described and illustrated with reference to a plurality of embodiments thereof, it is to be expressly understood that it is in no way limited to the disclosure of such preferred embodiments, but is capable of numerous modifications within the scope of the appended claims.

What is claimed is:

1. A hair treatment composition for giving hair a thicker appearance, consisting essentially of in water disodium cocoamphodiacetate, and at least one of inositol as a fat/sebum emulsifier, a surfactant, and a natural herb extract astringent cleansing substance.

2. The composition of claim 1 wherein the disodium cocoamphodiacetate is present at from 0.25% to 5% by weight.

3. The composition of claim 1 wherein there is present at least one of the following in the amounts indicated:

up to 2.0% by weight Panthenol,
up to 2.0% by weight Polysorbate 80,
up to 2.0% by weight Polyquarternium-11,
up to 2.0% by weight Inositol, and
up to 15% by weight of one or more natural herb extracts.

4. The composition of claim 3 wherein the aqueous base comprises approximately 70–80% by weight of the composition.

5. A hair treatment composition as claimed in claim 4 wherein the astringent is one or more of those selected from the group consisting of Nettle extract, Yarrow extract, Coltsfoot extract, Rosemary extract, Birch sap, Clover blossom extract, Birch leaf extract, Horsetail extract, and Sage extract.

6. A hair treatment composition as claimed in claim 4 further comprising glycerin.

7. A hair treatment composition as claimed in claim 2 further comprising up to 5% by weight of a glycol carrier selected from the group consisting of ethoxydiglycol, propylene glycol, and butylene glycol.

* * * * *